(12) United States Patent
Levin et al.

(10) Patent No.: US 10,441,620 B2
(45) Date of Patent: Oct. 15, 2019

(54) METHOD FOR PROTECTION OF BLADDER FROM DAMAGE

(71) Applicant: Wellstrong Biotech Co., Ltd., New Taipei (TW)

(72) Inventors: Robert M. Levin, Albany, NY (US); Dian Yu Lin, New Taipei (TW); Chang Chou Lan, New Taipei (TW); Chung Liang Lan, New Taipei (TW); Chung Min Lan, New Taipei (TW)

(73) Assignee: WELLSTRONG BIOTECH CO., LTD., New Taipei (TW)

( * ) Notice: Subject to any disclaimer, the term of this patent is extended or adjusted under 35 U.S.C. 154(b) by 0 days.

(21) Appl. No.: 15/711,938

(22) Filed: Sep. 21, 2017

(65) Prior Publication Data

US 2018/0078596 A1   Mar. 22, 2018

Related U.S. Application Data

(60) Provisional application No. 62/397,668, filed on Sep. 21, 2016.

(51) Int. Cl.
*A61K 36/00* (2006.01)
*A61K 36/48* (2006.01)

(52) U.S. Cl.
CPC .................................. *A61K 36/48* (2013.01)

(58) Field of Classification Search
None
See application file for complete search history.

(56) References Cited

U.S. PATENT DOCUMENTS

2005/0260288 A1* 11/2005 Lu ........................ A61K 33/00
424/725

FOREIGN PATENT DOCUMENTS

EP            1203771 A1 *  5/2002  ........... A61K 31/485

* cited by examiner

*Primary Examiner* — Qiuwen Mi
(74) *Attorney, Agent, or Firm* — Birch, Stewart, Kolasch & Birch, LLP

(57) ABSTRACT

The present invention is related to a method for protection of bladder from damage, and prevention of frequent urination using a *Canavalia ensiformis* supplement.

4 Claims, 4 Drawing Sheets

METHOD FOR PROTECTION OF BLADDER FROM DAMAGE

CROSS REFERENCE TO RELATED APPLICATIONS

This non-provisional application claims the benefit under 35 U.S.C. § 119(e) to U.S. Provisional Application No. 62/397,668, filed on Sep. 21, 2016, which is hereby expressly incorporated by reference into the present application.

FIELD OF THE INVENTION

The present invention is related to a method for protection of bladder from damage through a pretreatment with a *Canavalia ensiformis* supplement.

BACKGROUND OF THE INVENTION

Chemical cystitis may result from oral therapy with drugs such as cyclophosphamide, protamine sulfate, acetone, and from vesical instillation of various other chemical agents. One hypothesis concerning the etiology of various forms of cystitis relates to a defunctionalized and damaged bladder urothelial surface with subsequent penetration of substances in the urine into the bladder wall causing inflammation and increased permeability. Protamine sulfate has been used to effectively damage the mucin layer and urothelium of the bladder inducing cystitis. The addition of uric acid enhances the severity of the cystitis.

One of the major etiologies of the damage to the urothelium in chemical-induced models of cystitis is oxidative stress. Natural products showing antioxidant activity in several types of chemical cystitis have been shown to be effective in their treatment. It was reported that reduction of oxidative stress may play a role in the anti-inflammatory effect of the novel herbal formulation in a rat model of hydrochloric acid-induced cystitis (Bae, W. J. et al., *Neurourology and urodynamics* 34, 86-91, 2015). In addition, it was also disclosed that bladder oxidative stress and inflammation could be suppressed by a phytotherapeutic agent in a rat model of partial bladder outlet obstruction (Oka, M. et al., Suppression of bladder oxidative stress and inflammation by a phytotherapeutic agent in a rat model of partial bladder outlet obstruction, *The Journal of urology* 182, 382-390, 2009).

Some protection agents or therapeutic agents may be developed through the determination of ability to prevent protamine-uric acid induced cystitis of an animal urinary bladder.

SUMMARY OF THE INVENTION

It is unexpectedly discovered in the present invention that some herbal supplements or extracts have a good effect on protection of bladder from damage, and prevention of frequent urination.

Accordingly, one aspect of the present invention provides a method for protection of bladder from damage. The method comprises administering to a subject in need thereof an effective amount of a *Canavalia ensiformis* supplement.

In another aspect, the invention provides a method for prevention of frequent urination comprising administering to a subject in need thereof an effective amount of a *Canavalia ensiformis* supplement.

In one example of the invention, the *Canavalia ensiformis* supplement can be used in combination of a therapeutic agent or a substance that is effective in protection of bladder from damage, or prevention of frequent urination.

In yet aspect, the invention provides a pharmaceutical or dietary composition for protection of bladder from damage, or prevention of frequent urination comprising a *Canavalia ensiformis* supplement.

In further yet aspect, the invention provides a pharmaceutical or dietary composition for protection of bladder from damage, or prevention of frequent urination. The composition comprises a *Canavalia ensiformis* supplement in combination of an therapeutic agent or a substance that is effective in protection of bladder from damage, or prevention of frequent urination.

These and other objects, along with advantages and features of embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Figure 1:
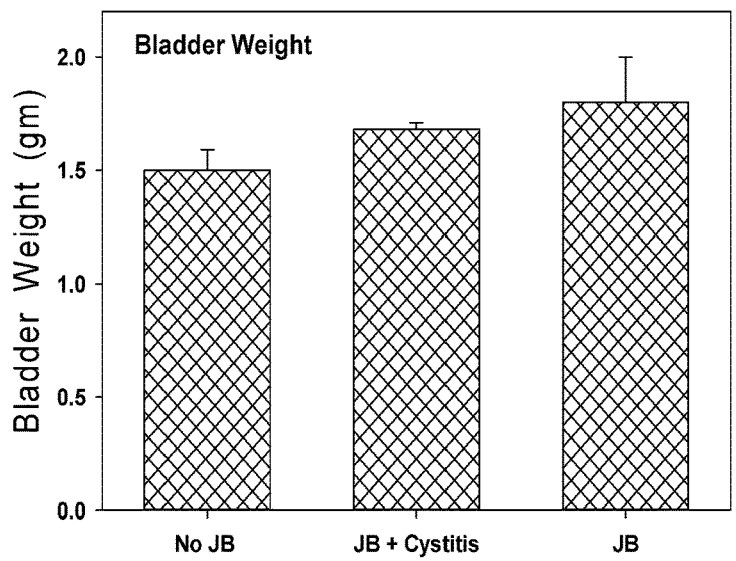
FIG. 1 shows the bladder weights for the groups, wherein there were no significant differences among the groups.

Unless defined otherwise, all technical and scientific terms used herein have the same meaning as commonly understood by a person skilled in the art to which this invention belongs.

It was found in the present invention that Jack Bean provides a good effect on the prevention of protamine-uric acid induced cystitis of the rabbit urinary bladder.

As used herein, the term "Jack Bean" or "JB" refers to the plant of *Canavalia ensiformis*, which is a legume that is used for human nutrition for a long time. *C. ensiformis* is a twining plant up to 1 meter (3.3 ft) in height. It has deep roots which makes it drought resistant and can spread via long runners. The flowers are pink-purple in colour and the pods can be up to 36 centimeters (14 in) in length with large white seeds. The young foliage is also edible.

Two of the major components of the Jack bean are urease and concanavalin A. Concanavalin A (ConA) is a lectin (carbonydrate-binding protein) and member of the legume lectin family. It binds specifically to certain structures found in various sugars, glycoproteins, and glycolipids. ConA is a plant mitogen which is known for its ability to stimulate mouse T-cells. It has also been found to be effective in the treatment of liver cancer and other tumors. Ureases, functionally, belong to the superfamily of amidohydrolases and phosphotriesterases. It is an enzyme that catalyzes the hydrolysis of urea into carbon dioxide and ammonia. These toxic properties have been completely eliminated by a proprietary methodology.

The term "*Canavalia ensiformis* supplement" as used herein refers to a product made from *Canavalia ensiformis*, including or not limited to its extract. The *Canavalia ensiformis* supplement may be prepared using standard or commonly used technology or methods in the art.

The present invention provides a method for protection of bladder from damage. The method comprises administering to a subject in need thereof an effective amount of a *Canavalia ensiformis* supplement.

On the other hand, the invention provides a method for prevention of frequent urination comprising administering to a subject in need thereof an effective amount of a *Canavalia ensiformis* supplement.

According to one example of the invention, the *Canavalia ensiformis* supplement can be used in combination of a therapeutic agent or a substance that is effective in protection of bladder from damage, or prevention of frequent urination.

Furthermore, the invention provides a pharmaceutical or dietary composition for protection of bladder from damage, or prevention of frequent urination comprising a *Canavalia ensiformis* supplement. The composition may further comprise an therapeutic agent or a substance that is effective in protection of bladder from damage, or prevention of frequent urination.

Example Effect of Jack Bean Supplement on In-Vivo Chemical Cystitis in Rabbits

Methods

All methods were approved by the IACUC Committee of the Stratton VA Medical Center, Albany, N.Y.

18 adult male NZW rabbits were divided into 3 groups of 6 rabbits each.

Group 1 were control rabbits. Each rabbit received cystometry before entering into the study and also at 1 and 2 weeks (end of the study).

Group 2 were rabbits given a placebo by gavage daily for 2 weeks prior to inducing cystitis and for 2 weeks following cystitis. Each rabbit received cystometry prior to entering into the study, immediately prior to inducing the cystitis, and at 1 and 2 weeks (end of the study) post cystitis.

Group 3 were rabbits given a suspension of the Jack Bean preparation (100 mg/ml) at 1 ml/kg by gavage daily for 2 weeks prior to inducing chemical cystitis and for 2 weeks following chemical cystitis. Each rabbit received cystometry prior to entering into the study, immediately prior to inducing the cystitis, and at 1 and 2 weeks post cystitis (end of the study).

The dose was chosen based on its use in animal studies. JB has been shown to have significant antioxidant activity using a variety of both in-vivo and in-vitro techniques. JB preparations have been utilized in traditional Chinese medicine to treat a number of conditions including cancer and diseases associated with oxidative stress with no side effects.

Immediately after the final cystometry, the bladder of each rabbit was excised rapidly and weighed. Four longitudinal strips (1×0.5 cm) were obtained from the bladder midventral side. The bladder strips included both muscle and mucosa layers. Each strip was mounted in a separate 15-ml bath containing Tyrode's solution containing glucose (1 mg/ml), maintained at 37° C. and equilibrated with a mixture of 95% oxygen and 5% carbon dioxide. An initial resting tension of 2 g was applied for 30 minutes, and the contractile responses were recorded isometrically using a force displacement transducer.

Each strip was stimulated by electrical field stimulation (FS) at 2, 8, and 32 Hz, 80 V and 1 ms duration. After FS, the maximal responses were determined sequentially for carbachol (20 mM), KCl (120 mM) and ATP (1 mM). A series of three washes at 15 minute intervals, with Tyrode's solution followed each of the pharmacologic stimulations.

The balance of the bladder was separated by blunt dissection into muscle and mucosa, frozen under liquid nitrogen and stored at −80° C. for biochemical analyses.

Cystometry:

Before chemical cystitis and also at 1 and 2 weeks following chemical cystitis each rabbit was sedated using ketamine/xylazine (25 mg/10 mg, im). The bladder was then catheterized under sterile conditions with an 8 F Foley catheter and the bladder emptied. A filling cystometrogram was performed using warmed saline at a filling rate of 2 ml per minute until a micturition contraction or overflow incontinence occurred. In general, each cystometry took approximately 30 minutes. Each cystometry was set to the volume at micturition=100% so that compliances could be normalized for differences in volume. The compliance is calculated as the rise in intravesical pressure over 20% of the curve on the plateau region.

Cystitis:

Immediately following cystometry, each rabbit was sedated with ketamine/xylazine (25 mg/10 mg, im). Under sterile conditions, the urinary bladder was catheterized with an 8 Fr. Foley catheter, emptied, and then filled with 25 ml of a saline solution containing protamine sulfate (10 mg/ml)+uric acid (100 mg/ml). The solution remained in the bladder for 30 minutes, the bladder was drained, and then washed three times with 50 ml of saline. The rabbits were allowed to recover for two weeks.

Contractile Studies:

After 2 weeks of cystitis, each rabbit received a final cystometry under sedation. Each rabbit was then euthanized and the bladder excised intact. Four full thickness longitudinal strips were then cut from the mid-bladder and placed in individual isolated baths containing 15 ml of an oxygenated Tyrodes physiological solution containing 1 mg/ml glucose. During a 30 minute period of equilibrium, 2 grams of tension were placed on each strip and they were then stimulated as follows: field stimulation at 2, 8, and 32 Hz, carbachol, ATP and KCl. After each drug stimulation, the bladder strips were rinsed with oxygenated warmed Tyrodes 3× at 15 minute intervals. Maximal contractile responses were recorded.

The balance of the bladder was separated into smooth muscle and mucosal tissues, frozen under liquid nitrogen and stored at −80° C. for later biochemical studies.

CUPRAC Assay for Total Antioxidants:

The CUPRAC assay was utilized to determine the total antioxidant capacity. This assay relies on the electron donating capabilities of antioxidants to reduce the copper ion. The CUPRAC working solution consisted of 10 mM copper (II) chloride dihydrate, 1M ammonium acetate, and 7.5 mM neocuproine. 0.15 mL of the above three solutions were added to 0.15 mL of each sample and allowed to react for 30 minutes at room temperature, after which the absorbance was read at 450 nm in a Hitachi U-2001 spectrophotometer.

Statistical Analysis:

Each set of data was analyzed individually. One way analysis of variance was used followed by the TUKEY test for individual differences among the groups; $p<0.05$ was required for statistical significance. For all studies, there was an N=6.

Results

In the example, a Jack Bean supplement was evaluated for its ability to reduce or prevent the dysfunctions induced by experimental cystitis. As mentioned previously, we induced the cystitis by placing 25 ml saline containing protamine sulfate (10 mg/ml)+uric acid (100 mg/ml) in the bladder via 8 F catheter for 30 minutes. Three groups of rabbits were utilized. As shown in FIG. 1, the first group were control rabbits treated without cystitis (No JB); the second group were rabbits that received cystitis at two weeks, and allowed to survive an additional two weeks (JB+Cystitis); and the third were treated for 2 weeks prior to cystitis with JB and for two weeks following cystitis (JB). The control group had no treatments. As shown in FIG. 1, no significant differences in the bladder weights among the three groups were found.

Figure 2:
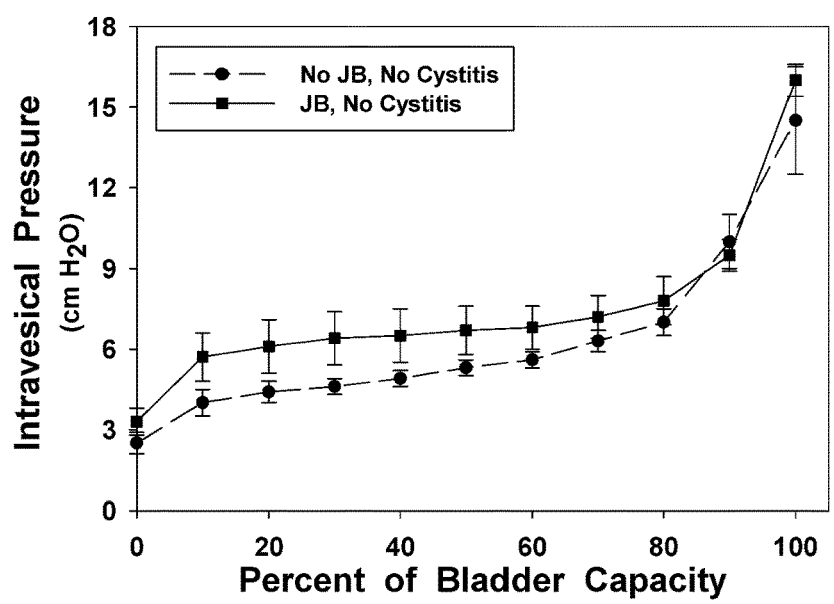
FIG. 2 shows the cystometries for both groups prior to cystitis, wherein the both groups had similar bladder capacities, and the group treated with JB was found to provide a significantly lower compliance than the group treated without JB.
Figure 3:
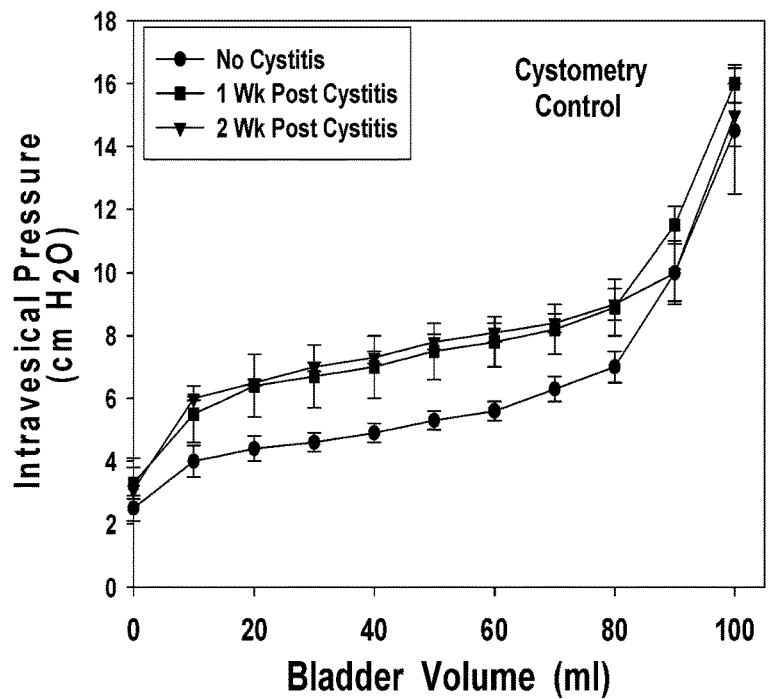
FIG. 3 shows the cystometries for no cystitis, and at 1 and 2 weeks following cystitis (without JB). At 1 and 2 weeks following cystitis no significant decreases in compliance and in bladder capacity were found.
Figure 4:
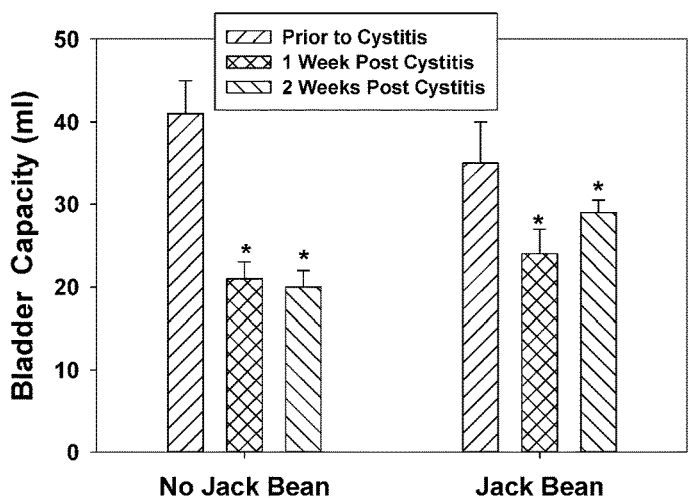
FIG. 4 shows the bladder capacities for the different groups, wherein no significant and similar decreases in bladder capacity in all the groups were found at both one and two weeks post cystitis.
Figure 5:
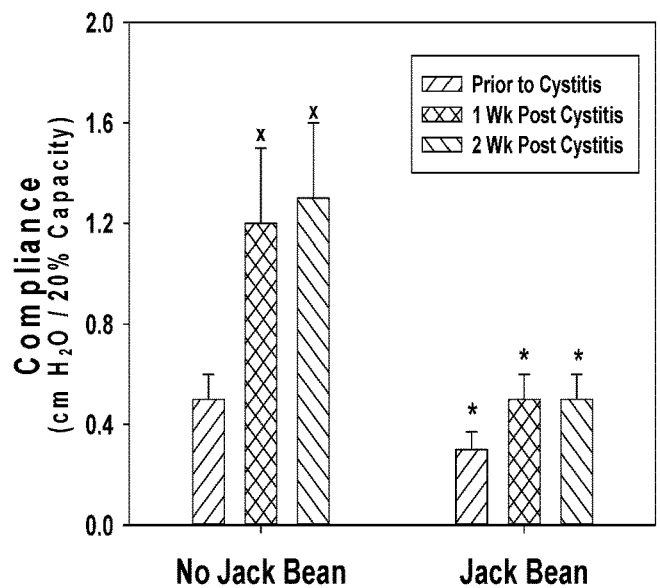
FIG. 5 shows the compliance for all groups, wherein an increase was found in the compliance number, which represents an increase in the stiffness of the bladder and thus a decrease in the true compliance. For the group treated without JB, no significant decreases were observed in compliance at both 1 and 2 weeks post cystitis. For the JB group, there were significant decreases in compliance when compared to the group treated without JB for both pre and post cystitis groups. Although there were slight increases in the group treated with JP post cystitis, these increases did not reach statistical significance.
Figure 7:
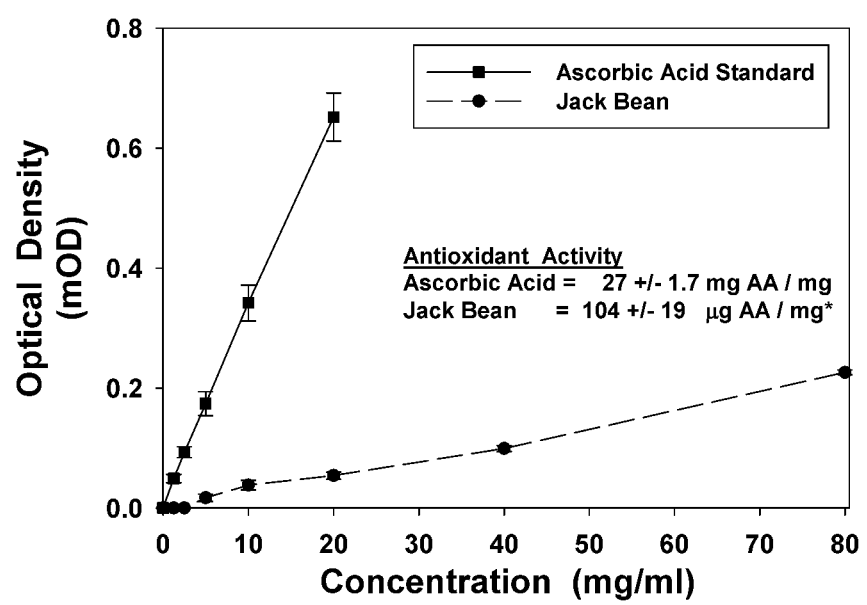
FIG. 7 shows the total antioxidant activity for the ascorbic acid standard and for the JB group. The curves were linear with an antioxidant value of 27±1.7 mg Ascorbic acid per mOD optical density for the standard, and 104±19 g AA units/mg JB.

As shown in FIG. 2, although no significant differences in bladder capacity among the three groups, the JB curve had a significantly lower compliance than the no JB curve (less stiff). As shown in FIG. 3, at 1 and 2 weeks following cystitis, significant decreases in compliance and in bladder capacity were found. As shown in FIG. 4, cystitis resulted in similar significant decreases in bladder capacities in both groups, and the cystometry demonstrated clearly that cystitis+/−JB resulted in a decreased bladder capacity. As shown in FIG. 5, the compliance for the JB group for prior to cystitis and for 1 or 2 weeks post-cystitis were significantly lower than the JB group, whereas cystitis induced a significant decrease in compliance in the control cystitis group at both one and two weeks, no changes in the compliance in the group treated with JB (JB) at either 1 or 2 weeks following cystitis. As shown in FIG. 7, the total antioxidant activity of the JB group showed significant antioxidant activity as compared with the ascorbic acid standard.

Figure 6:
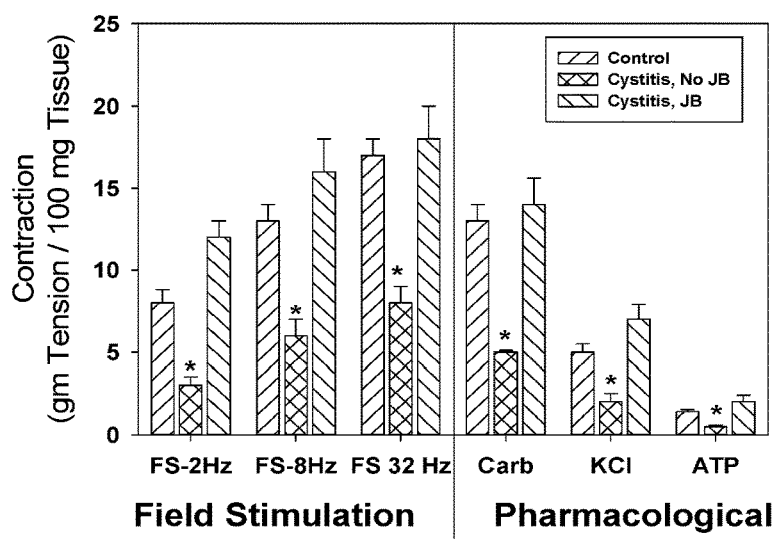
FIG. 6 shows the contractile responses to all forms of stimulation. Cystitis in the absence of JB resulted in significant decreases to all form of stimulation when compared to the group treated without JB. However, pretreatment with JB completely protected the bladder from contractile dysfunctions.

In regard to the contractility studies, control cystitis induced significant decreases in the responses to all forms of stimulation. As shown in FIG. 6, at 2 weeks post cystitis, the contractile responses to all form of stimulation were significantly reduced from Control JB. A field stimulation requires the following sequence of events: 1) Stimulation of post-synaptic membranes to release acetylcholine and ATP. 2) Diffusion across the synaptic cleft and stimulation of the post-synaptic muscarinic cholinergic and purinergic receptors. 3) Stimulated release of $Ca^{++}$ from the sarcoplasmic reticulum (for muscarinic stimulation) and from extracellular sites (for both muscarinic and purinergic stimulation) through calcium channels into the smooth muscle cell. 4) Activation of the smooth muscle components to contract. 5) Both muscarinic and purinergic receptor activation and smooth muscle contraction require energy from the breakdown of ATP to ADP+Pi. Interference with any of these 5 factors would result in a decrease in the contractile force.

In regard to the pharmacological responses: for carbachol, there is no release or diffusion of neurotransmitters, nor is there participation of purinergic neurotransmission. However steps 2-5 are all required. In regard to ATP, there is no release or diffusion of neurotransmitters, nor is there participation of cholinergic neurotransmission or release of calcium from the SR. However steps 2-5 are all required. In response to KCl, for step 3 there is no release of $Ca^{++}$ from the sarcoplasmic reticulum but steps 4 and 5 are required.

For all form of stimulation, JB administration prevented all contractile dysfunctions induced by cystitis. This would indicate that the mechanisms listed above (1-5) were all protected.

SUMMARY

The observed decrease in bladder volume at micturition could be caused by a variety of processes. First, cystitis would damage the glycosaminoglycan layer which would allow urine solutes to enter the bladder. These could sensitize the sensory receptors in the urothelium to stimulate a micturition reflex at lower intravesical volumes than the volumes required to stimulate micturition in the control bladders. Second, cystitis could result in damage to the sarcoplasmic reticulum which would lead to increased release of $Ca^{++}$ which in turn would result in increased smooth muscle tension with bladder filling (increase in bladder stiffness and decreased compliance) thus reaching the intravesical pressure that initiates micturition at relatively low intravesical volumes. In man, cystitis often results in both decreased volume at micturition, and decreased bladder compliance. Another result of cystitis would be damage to the mitochondria that provide the metabolic energy to the cell in the form of ATP. Decreases in ATP would result in contractility dysfunction resulting in decreased contractile force, as was seen in the cystitis group without JB.

Experimental cystitis resulted in decreased compliance, decreased volume at micturition, and decreased contractile responses to all forms of stimulation. These results indicate that the cystitis resulted in pathological damage to the bladder mucosa, sarcoplasmic reticulum, mitochondria, and smooth muscle fibers which remained constant for the two week post-cystitis period. The observed decreased volume at micturition could be a result of one or several factors as mentioned above, not all of them pathological. The significantly decreased compliance in the cystitis-no treatment group shows a pathologic response to the cystitis as given above. The protective effect of JB on compliance indicates strongly that this pre-treatment protected the bladder from damage to the sarcoplasmic reticulum.

The contractile response to the pharmacological agents (carbachol, ATP and KCl) indicates strongly that JB pre-treatment protected the bladder from damage to mitochondria and the smooth muscle fibers. In regard to field stimulated contraction, JB fully protected the response to all frequencies of stimulation indicates that JB did fully protected against damage to the synaptic connection between the pre-synaptic nerves and the post-synaptic muscarinic and purinergic receptors.

CONCLUSION

Cystitis resulted in decreased compliance, decreased volume at micturition, and decreased contractile responses to all forms of stimulation. These results indicate that the protamine sulfate-uric acid cystitis resulted in patho-physiological damage to the bladder mucosa, sarcoplasmic reticulum, mitochondria, and smooth muscle fibers which remained constant for the two week post-cystitis period. The protective effect of JB on compliance indicates strongly that this pre-treatment protected the bladder from damage to the sarcoplasmic reticulum, mitochondria, and cell membrane.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any appropriate suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A method for protection of bladder from damage induced by cystitis, comprising administering to a subject in need thereof an effective amount of a *Canavalia ensiformis* supplement.

2. A method for prevention of frequent urination induced by cystitis, comprising administering to a subject in need thereof an effective amount of a *Canavalia ensiformis* supplement.

3. The method of claim 1, wherein the *Canavalia ensiformis* supplement is administered in combination with a therapeutic agent or a substance that is effective in protection of bladder from damage, or prevention of frequent urination.

4. The method of claim 2, wherein the *Canavalia ensiformis* supplement is administered in combination with a therapeutic agent or a substance that is effective in protection of bladder from damage, or prevention of frequent urination.

* * * * *